United States Patent [19]

Tomiyama et al.

[11] Patent Number: 5,583,641
[45] Date of Patent: Dec. 10, 1996

[54] BONDING WIRE HEIGHT DETECTION METHOD

[75] Inventors: Hiromi Tomiyama, Musashimurayama; Takeyuki Nakagawa, Akishima; Satoru Nagai, Iruma, all of Japan

[73] Assignee: Kabushiki Kaisha Shinkawa, Tokyo, Japan

[21] Appl. No.: 525,282

[22] Filed: Sep. 8, 1995

[30] Foreign Application Priority Data

Sep. 9, 1994 [JP] Japan .................................. 6-240789

[51] Int. Cl.$^6$ ............................................. G01B 11/00
[52] U.S. Cl. ...................... 356/372; 356/384; 250/559.34
[58] Field of Search .................................. 356/372, 376, 356/384; 250/559.34

[56] References Cited

U.S. PATENT DOCUMENTS 4,942,618  7/1990  Sumi et al. ............................. 356/384
5,030,008  7/1991  Scott et al. ............................. 356/376
5,347,362  9/1994  Sugawara ................................. 356/372

*Primary Examiner*—F. L. Evans
*Attorney, Agent, or Firm*—Koda And Androlia

[57] ABSTRACT

A method for evaluating the height of a wire bonded between a semiconductor chip and a lead frame including the steps of: investigating the correlation between wire height and wire width beforehand by shifting the focusing level of an optical system, setting a detection level which is the focusing level of the optical system based upon an upper limit level and a lower limit level which are to be the standard levels for the height of the wire to be detected. The acceptability of the height of the wire is judged by ascertaining whether or not the imaged width of the wire is within the wire width range which is between the upper and lower limit levels of the correlation between the wire height and the wire width.

1 Claim, 4 Drawing Sheets

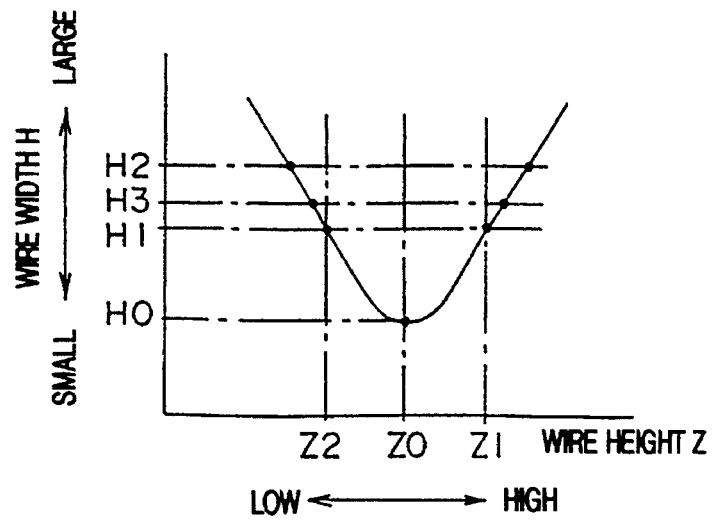
FIG.2
FIG.3(a)
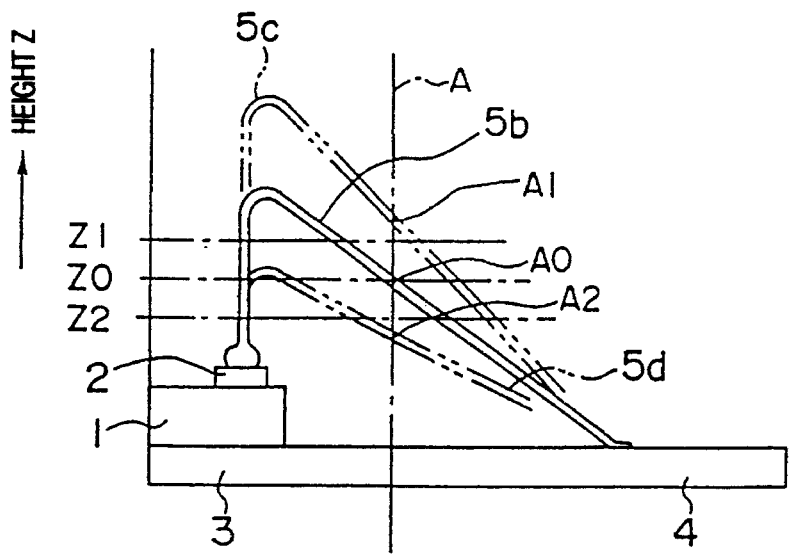
FIG.3(b)
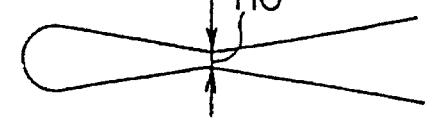
FIG.3(c)
FIG.3(d)
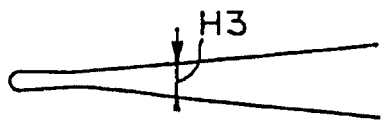

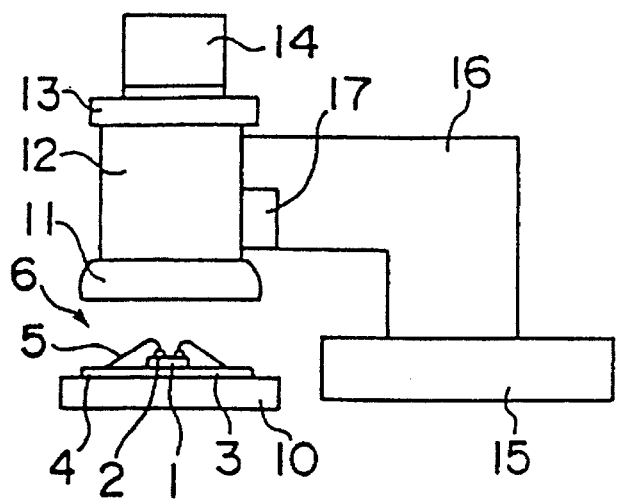
FIG.5
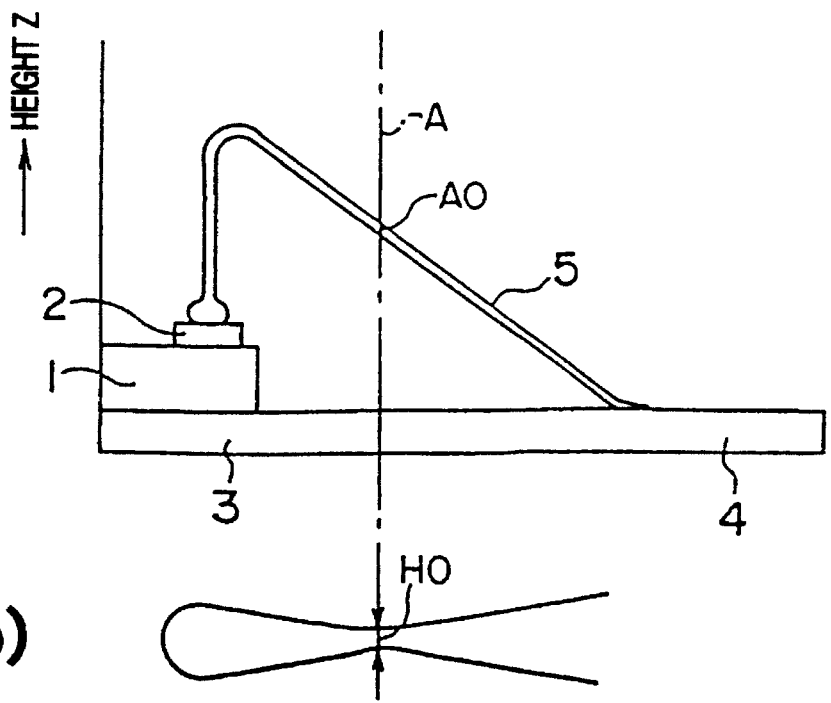
FIG.6(a)
FIG.6(b)

BONDING WIRE HEIGHT DETECTION METHOD

BACKGROUND OF THE INVENTION

1. Field of the Invention

The present invention relates to a method for detecting the height of wires bonded between the pads of semiconductor chips and the leads of lead frames.

2. Prior Art

The method disclosed in U.S. Pat. No. 5,347,362 which corresponds to Japanese Patent Application Laid-Open (Kokai) No. 5-160233 is an example of a conventional method for detecting the height of bonded wires. FIG. 5 shows an apparatus in which this method is used.

In this prior art method, a workpiece 6 in which wires 5 are bonded so as to connect the pads 2 of a semiconductor chip 1 and the leads 4 of a lead frame 3 is placed on a detection stand 10. An illuminating means 11 is positioned above the workpiece 6 which is placed on the detection stand 10. The illuminating means 11 is mounted to the lower part of an optical system 12, which includes lenses and prisms, and an imaging device 14, which is, for example, a CCD (photoelectric transducer element) camera, is mounted to the upper part of the optical system 12 with a diaphragm means 13 in between. The optical system 12 to which the illuminating means 11 and the imaging device 14 are mounted is disposed on a supporting block 16 which is fastened to the surface of an XY table 15. The optical system 12 is moveable up and down by a Z-axis motor 17.

Although not shown in FIG. 5, the illuminating means 11 includes a high-angle illuminating device and a low-angle illuminating device. In the high-angle illuminating device, LED's are disposed in the form of a ring; and in the low-angle illuminating device, LED's are likewise disposed in the form of a ring so that the LED's of the low-angle illuminating device surround the LED's of the high-angle illuminating device. The respective LED's of the high-angle illuminating device and low-angle illuminating device are oriented toward the axial center of the optical system 12. Furthermore, the angle of inclination of the high-angle illuminating device relative to a horizontal plane is set to be approximately 30 to 55 degrees, and the angle of inclination of the low-angle illuminating device relative to the horizontal plane is approximately 5 to 15 degrees.

When the height of a bonded wire is detected, the low-angle illuminating device of the illuminating means 11 is controlled so that, as disclosed in the above-identified prior art, some of the LED's are switched off; and the detection is performed with the focal depth set at a shallow depth using the diaphragm means 13.

More specifically, the XY table 15 shown in FIG. 5 is driven so that the optical system 12 is positioned, as seen in FIG. 6(a), on a vertical line A which passes through the XY coordinates of the wire 5 that is to be detected. Then, the Z-axis motor 17 is driven so that the optical system 12 is raised or lowered, and focusing of the imaging device 14 is made on the detection point A0, thus obtaining the image of the wire 5. The obtained image appears as shown in FIG. 6(b). In FIG. 6(b), the width H0 of the wire appears to be a minimum at the focal point A0 (detection point A0), and the wire width appears to become larger and less distinct as the distance from the focal point A0 increases. As disclosed in the prior art as well, there is a particular relationship between the blurring width (wire width) and the wire height. Accordingly, by knowing this relationship beforehand, it is possible to calculate the height at an arbitrary point of the wire from the obtained wire width.

In the prior art described above, the height of a bonded wire is measured based upon the imaged wire width using the in-focus wire image as a standard. However, there is no disclosure in this prior art concerning the method used to evaluate (i.e., ascertain the acceptability of) the measurement results.

SUMMARY OF THE INVENTION

Accordingly, the object of the present invention is to provide a wire height detection method which makes it possible to evaluate the height of bonded wires.

The object of the present invention is accomplished by a unique step taken in a bonding wire height detection method in which the height of a wire bonded between a pad of a semiconductor chip and a lead of a lead frame is detected by imaging the wire by an imaging device through an optical system, and the unique step according to the present invention is that the correlation between wire height and wire width is investigated beforehand by varying the focusing levels of the optical system, then the detection level (which is the focusing level of the optical system) is set based upon an upper limit level and a lower limit level which are the standard values for the height of the wire to be detected, and finally a determination is made as to whether the imaged width of the wire detected is within the wire width range that is defined between the upper limit level and lower limit level in the correlation between the wire height and the wire width, thus ascertaining the acceptability (pass or failure) of the height of the wire bonded.

Generally, when the focal point of the optical system coincides with the wire detection point, the wire width at the detection point appears to be the minimum; and as the focal point of the optical system is moved from the detection point, the wire width becomes larger and less distinct. With this in mind, the correlation between the wire height and wire width is investigated beforehand; and then the wire is detected with the detection level of the optical system set based upon the upper limit value and the lower limit value which are standard values for the height of the wire being detected. If the detected wire width is smaller than the wire width corresponding to the upper and lower limit levels for the wire height, the wire height is judged as "passing" or not defective; however, if the detected wire width is larger than the wire width that corresponds to the upper and lower limit values, the wire height is judged as "failing" or defective.

BRIEF DESCRIPTION OF THE DRAWINGS

FIG. 2 is a graph showing the correlation between wire width and wire height;

FIG. 3 shows the relationship between wire height and wire width, wherein FIG. 3(a) is a front view of wires of different heights, while FIGS. 3(b), 3(c) and 3(d) show images of wires of different heights;

FIG. 5 is a schematic side view of a bonding wire height detection device used in the method of the present invention and of the prior art;

FIG. 6 illustrates the relationship between wire height and wire width in the detection of prior art, wherein FIG. 6(a) is a from view of the wire, while FIG. 6(b) shows the imaged wire width.

DETAILED DESCRIPTION OF THE INVENTION

One embodiment of the present invention will be described below with reference to FIGS. 1 through 5. In this embodiment, the detection is performed using the detection apparatus shown in FIG. 5.

Figure 1:
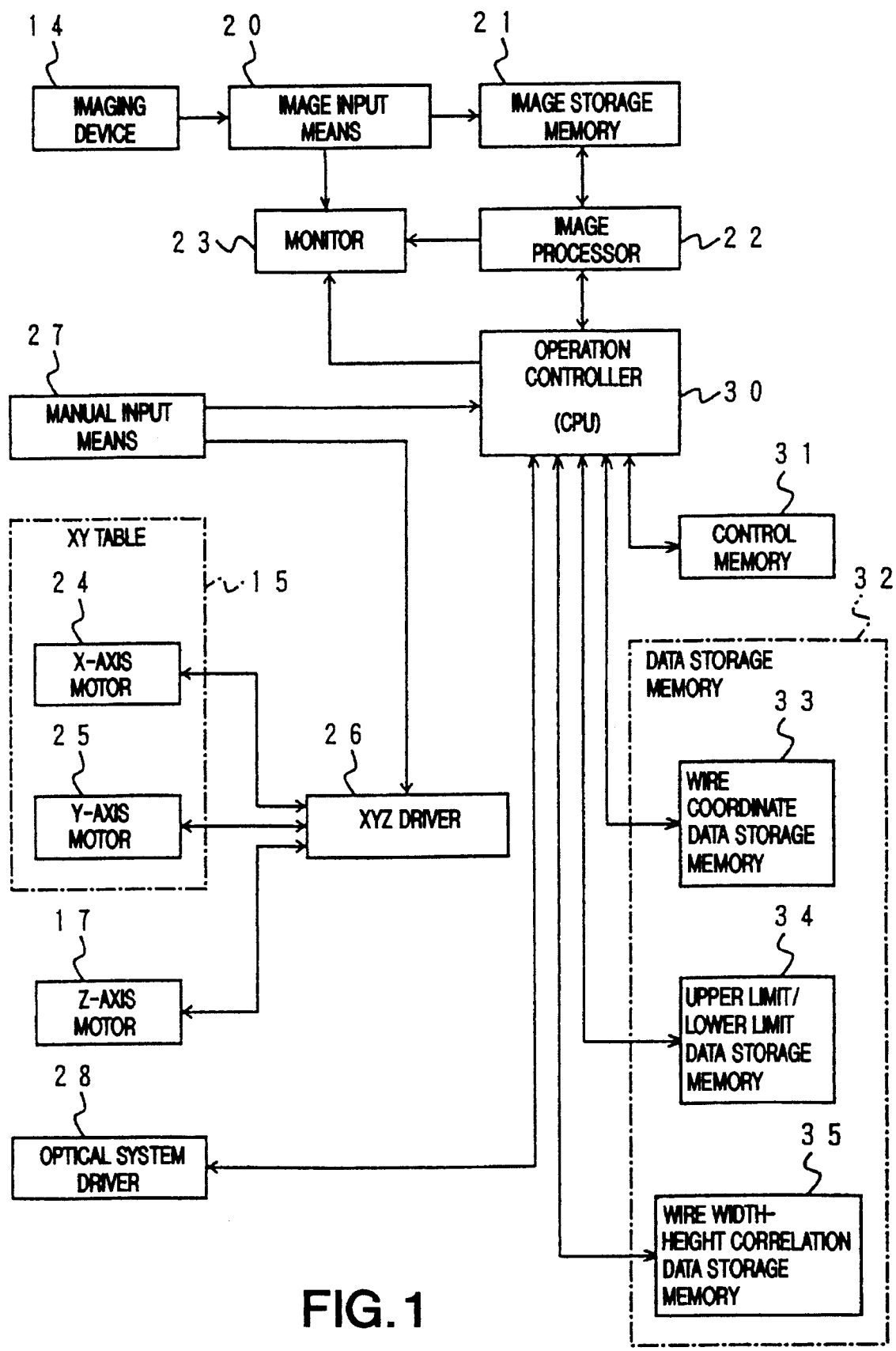
FIG. 1 is a block diagram of one embodiment of the control circuitry used in the bonding wire height detection method of the present invention.

As shown in FIG. 1, an image of a wire obtained by the imaging device 14 in FIG. 5 is converted into digital signals by an image input means 20 and stored in an image storage memory 21. The image patterns stored in the image storage memory 21 are subject to image processing by an image processor 22, and the resulting image is displayed on a monitor 23. An X-axis motor 24 and a Y-axis motor 25 which drive the XY table 15 are controlled along with a Z-axis motor 17 by an XYZ driver 26. The XYZ driver 26 can be directly controlled by a manual input means 27 or by an operation controller 30. The setting of the optical system driver 28 (which includes the diaphragm means 13 and illuminating means 11, etc. as shown in FIG. 5) is also controlled by the operation controller 30.

The operation controller 30 controls the image processing and various parts of the inspection apparatus in accordance with processing procedures stored in a control memory 31. In addition to controlling the XYZ driver 26 and optical system driver 28, the operation controller 30 calculates the wire width so as to ascertain the acceptability of the wire height, etc. based upon the images processed by the image processor 22. In addition, the operation controller 30 reads out and processes the required data from a data storage memory 32 and, in addition, stores the calculated data in the data storage memory 32. The data storage memory 32 includes: a wire coordinate data storage memory 33 which stores the XY coordinates of the wires 5 being detected, an upper limit/lower limit data storage memory 34 which stores the upper and lower limit values that are used as standards for the acceptability of the wire height, and a wire width-height correlation data storage memory 35 which stores data indicative of the correlation between the wire width and height. The coordinates and the upper and lower limit levels for the wire to be detected are stored beforehand in the wire coordinate data storage memory 33 and upper limit/lower limit data storage memory 34, respectively.

The operation of the above embodiment will be described below.

Prior to the wire height detection, the correlation between the wire height and the wire width is investigated. This is done in the following steps:

a. The iris of the diaphragm means 13 of the optical system driver 28 and the illumination level of the illuminating means 11 are set to conditions that are suitable for wire height detection as in the prior art.

b. A workpiece 6 on which the wire 5 is correctly installed and bonded is placed on the detection stand 10.

c. The manual input means 27 is operated so that the X-axis motor 24 and Y-axis motor 25 are driven by the XYZ driver 26, thus moving the XY table 15 so that the optical system 12 is positioned above the detection point of the wire that is to be detected.

d. The manual input means 27 is further operated so that the Z-axis motor 17 is driven a fixed amount at a time via the XYZ driver 26, i.e., so that the level of the focal point is shifted by the movement of the optical system 12 a fixed amount at a time and that the images obtained by the imaging device 14 are processed by the operation controller 30, thus detecting the wire width.

e. The correlation between the height of the optical system 12 (i.e., the wire height Z) and the wire width H of the wire correctly bonded is determined, and this correlation is stored in the wire width-height correlation data storage memory 35.

In FIG. 3(a), Z0 represents the detection level (focusing level of the optical system 12), Z1 represents the upper limit level, and Z2 represents the lower limit level; in addition, A indicates a vertical line passing through the coordinates of the wire 5 being detected. In FIG. 2, H0 represents the wire width at the detection level Z0, H1 represents the wire width at the upper limit level Z1 and at the lower limit level Z2.

Figure 4:
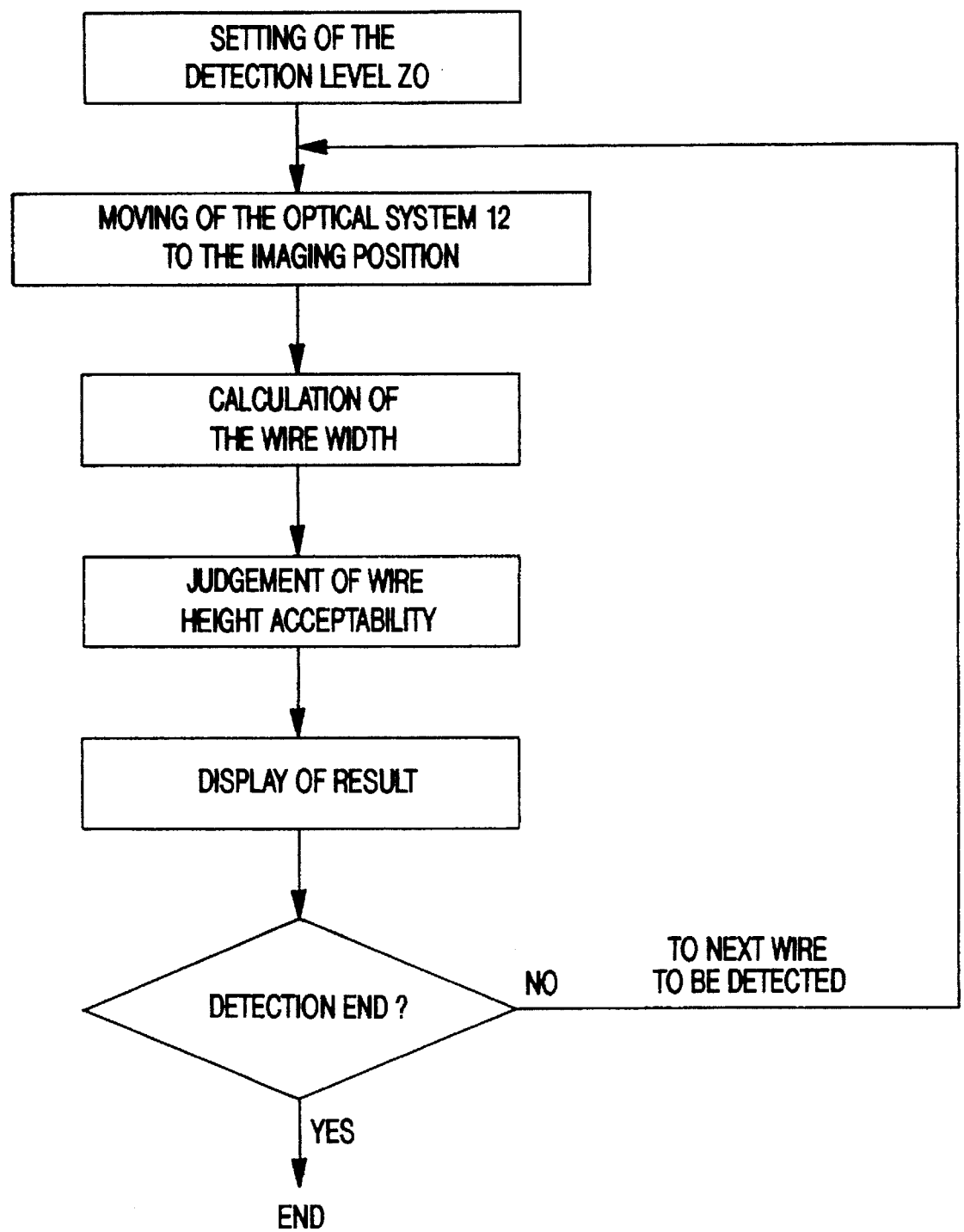
FIG. 4 is a flow chart showing the steps of operation of the wire height detection according to the present invention.

When the workpiece 6 to be detected is placed on the detection stand 10, an evaluation of the wire height is performed as shown in FIG. 4.

1. First, the operation controller 30 sets the detection level Z0 of the optical system 12 based upon the upper limit value Z1 and lower limit value Z2 which are stored in the upper limit/lower limit data storage memory 34 using the mean or averaged value of the upper limit level Z1 and the lower limit level Z2 which is obtained by Equation 1 shown below:

EQUATION 1

$$Z0=(Z1+Z2)/2$$

2. Then, the Z-axis motor 17 is driven by the XYZ driver 26 so that the optical system 12 is positioned at this detection level Z0 ("setting of the detection level Z0" step).

3. Next, the operation controller 30 reads out the wire coordinate data stored in the wire coordinate data storage memory 33 and drives the X-axis motor 24 and Y-axis motor 25 via the XYZ driver, thus moving the XY table 15 so that the optical system 12 is moved to the detection center line A of the wire to be detected ("moving of the optical system 12 to the imaging position" step).

4. Then, an image of the wire is taken by the imaging device 14, and the wire width resulting from the processing of this image by the image processor 22 is calculated by the operation controller 30 ("calculation of the wire width" step).

5. The operation controller 30 calculates the wire height which is stored in the wire width-height correlation data storage memory 35 and which corresponds to the calculated wire width, and then the controller 30 ascertains whether or not this wire height is within the range of the upper limit level Z1 and lower limit level Z2 stored in the upper limit/lower limit data storage memory 34 ("judgement of wire height acceptability" step).

6. The result of the judgement is displayed on the monitor 23 ("display of result" step).

In FIG. 3, 5b represents a normal or correctly bonded wire, 5c represents a wire which exceeds the upper limit level Z1, and 5d represents a wire which is below the lower limit level Z2. In addition, the respective intersection points between the vertical line A that passes through the coordinates of the wire 5 and the wires 5b, 5c and 5d are indicated by A0, A1 and A2, respectively.

In the case of wire 5b, as shown in FIG. 3(b), the wire width calculated by the operation controller 30 is H0, and this value H0 is smaller than H1 as seen from FIG. 2; and therefore, it falls within the range between the upper limit value Z1 and lower limit value Z2. Accordingly, the wire 5b is judged as "passing (not defective)".

Meanwhile, in the case of wires 5c and 5d, as shown respectively in FIGS. 3(c) and 3(d), the wire widths calculated by the operation controller 30 are H2 and H3, respectively; and these widths H2 and H3 are, as seen from FIG. 2, larger than H1 (in other words, H2 and H3 are located above H1 in FIG. 2), and they are located outside the range between the upper limit level Z1 and lower limit level Z2. Accordingly, the heights of wires 5c and 5d are judged as "failing (defective)". In other words, the wire 5c is too high and the wire 5d is too low; and therefore, they are not properly bonded.

As seen from the above, in the present invention, the correlation between the wire height and the wire width is investigated beforehand by shifting the focusing level of the optical system, and the detection level (which is the focusing level of the optical system) is set on the basis of an upper limit level and a lower limit level which are to be standard values for the height of the wires to be detected. For each wire to be detected, the acceptability of the wire height is judged by ascertaining whether or not the imaged wire width is within the wire width range which is between the upper and lower limit levels. It is thus possible to evaluate the height of bonded wires.

We claim:

1. A bonding wire height detection method in which a height of a wire bonded to a pad of a semiconductor chip and a lead of a lead frame is detected by imaging said wire by an imaging device through an optical system, said method being characterized in that: a correlation between a wire height and a wire width is investigated beforehand by shifting a focusing level of said optical system; a detection level which is a focusing level of said optical system is set based upon an upper limit level and a lower limit level which are standard values for the height of a wire to be detected; and an acceptability of a wire height is ascertained by determining whether an imaged width of a wire detected is within a wire width range located between said upper limit level and said lower limit level in said correlation between said wire height and wire width.

* * * * *